Figure 1:
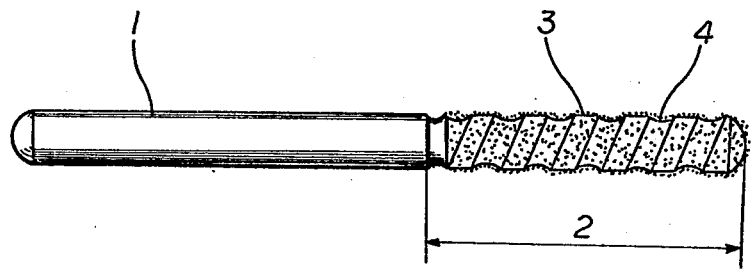

United States Patent [19]

Plischka

[11] Patent Number: 4,466,795
[45] Date of Patent: Aug. 21, 1984

[54] HELICOIDALLY GROOVED DENTAL BURR

[75] Inventor: Gerhard Plischka, Graz, Austria

[73] Assignee: Dendia-Werk Dr. Ing. Hans O. Scheid Gesellschaft M.B.H., Vienna, Austria

[21] Appl. No.: 420,248
[22] PCT Filed: Dec. 29, 1981
[86] PCT No.: PCT/AT81/00033
    § 371 Date: Sep. 13, 1982
    § 102(e) Date: Sep. 13, 1982
[87] PCT Pub. No.: WO82/02827
    PCT Pub. Date: Sep. 2, 1982

[30] Foreign Application Priority Data

Feb. 17, 1981 [AT] Austria ................................... 730/81

[51] Int. Cl.³ .............................................. A61C 3/06
[52] U.S. Cl. ................................................. 433/166
[58] Field of Search .................. 433/166, 165; 51/204, 51/208

[56] References Cited

U.S. PATENT DOCUMENTS 4,058,898 11/1977 Nash .................................... 433/166
4,389,192 6/1983 Neuwirth ............................ 433/166

Primary Examiner—Robert Peshock
Attorney, Agent, or Firm—Karl F. Ross

[57] ABSTRACT

A dental burr to be used in a clockwise-rotating chuck of a drilling machine has a generally cylindrical or conical working surface, coated with abrasive particles (diamonds), which forms a flat helicoidal strip of left-handed pitch whose width substantially equals that of an intervening continuous groove.

5 Claims, 2 Drawing Figures

HELICOIDALLY GROOVED DENTAL BURR

This invention relates to a diamond grinding element with diamonds secured to the operative surface, wherein the grinding element displays a cylindrical or conical basic shape. Such grinding elements have application in dentistry and dental technology. A wide range of diamond grinding elements is in use, such as ball, conical, or cylinder and wheel shapes with concentric uniform surfaces. In addition, combination shapes such as cylinders with conical points, pear shapes or cones with ball-shaped points are encountered. Perforated disks have been in use for a number of years and are considered as the first step in achieving more effective cooling of the surface to be treated.

Another diamond grinding element, especially for application in bone treatment, is elongated, conical and pointed, with three clockwise grooves upon the diamond coated surface which serve for more effective cooling and for improved removal of the abraded material from the bone fissure. The bone drills, however, are not operated at the high (e.g. over 100,000) rpm customary in the treatment of dental substances.

Other familiar grooved, cylindrical diamond instruments grind furrows into the dental substance to be removed, which must then be levelled by an old-type conventional diamond instrument.

The object of the invention is to create a diamond grinding element of the type mentioned above in such a way that effective thermal dissipation and efficient removal of the abraded material can be achieved through flushing. In addition, the treated surface should not show any rough grooves.

The invention achieves this purpose in that the operative surface [of the grinding element] is formed by a counter-clockwise band within the cylindrical or conical basic shape. By means of this counter-clockwise screw-like band on the diamond grinding element under application, a number of advantages are gained: the operative grinding element surface of the instrument assures a constant alternation of the contact zones through its counter-clockwise form, as well as free thermal dissipation and effective removal of the abraded material through rapidly alternating flushing. Further, the treatment of the affected surface does not produce grooves but rather a non-grooved form with uniform shear, whereby a subsequent treatment—apart from the usual one required by roughening to the depth of the diamond granule—is eliminated. The relatively small surface in grinding contact requires only a minimal pressure for optimal grinding efficiency. In addition, the instrument under application does not display grinding edges either easily worn or subject to extreme pressures and also shows a decreased tendency toward oscillation.

The counter-clockwise modular thread band form under application also enhances the distribution of the required cooling fluid (spray) into inaccessible places during use up to the point of the instrument, when the machine is rotating clockwise.

As a result of the left-hand twist of the band-like grinding surface, the diamond instrument under application is forced into the chuck during the grinding process with machines normally turning to the right, as a result of which slippage out of the chuck is impeded even with decreased retention power of the chuck.

The invention will be more clearly understood upon consideration of the drawing of two variations of the module.

Figure 2:
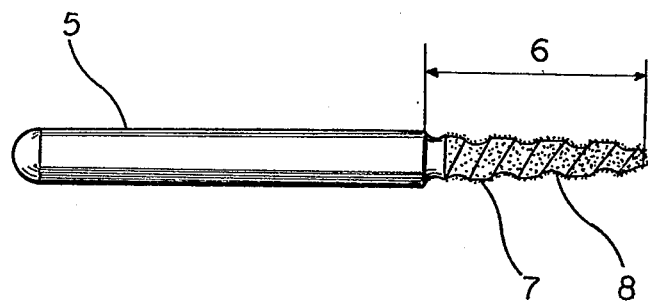

FIGS. 1 and 2 show a cylindrical and a conical diamond grinding element.

The cylindrical diamond grinding element 1, made of NIRO-steel, as shown in FIG. 1, is provided with a counter-clockwise band 3 on its operative surface 2 between the grooves 8 which, as a result of the conical form of the section, run as a spiral with surface 6, so that the diameters of the band sections, as they approach the point, are smaller than those sections preceding them.

The invention is not limited to the examples given and the grinding elements can have various basic shapes or, as in the case of wheels, can provide for the application of a spiral surface. Instruments will most commonly have the basic form of a cylinder or of a cone with various angular inclinations.

I claim:

1. A dental burr having an elongate body centered on an axis, said body having a shank engageable by a chuck of a drilling machine rotating clockwise as viewed toward a tip of said body, a portion of said body between said shank and said tip having a working surface formed with a flat helicoidal strip of left-handed pitch terminating at said tip, said strip having a multiplicity of turns separated by turns of a continuous helicoidal groove.

2. A dental burr as defined in claim 1 wherein said portion is cylindrical.

3. A dental burr as defined in claim 1 wherein said portion is conical.

4. A dental burr as defined in claim 3 wherein said portion has a cone angle between about 2° and 5°.

5. In combination, a dental burr having an elongate body forming a shank, and a drilling machine provided with a chuck engaging said shank for setting said burr in clockwise rotation as viewed toward a tip of said body, the improvement wherein a portion of said body lying between said shank and said tip has a working surface formed with a flat helicoidal strip of left-handed pitch terminating at said tip, said strip having a multiplicity of turns separated by turns of a continuous helicoidal groove.

* * * * *